US00PP13328P2

(12) United States Plant Patent
Kobayashi

(10) Patent No.: US PP13,328 P2
(45) Date of Patent: Dec. 10, 2002

(54) POINSETTIA PLANT NAMED 'ECKALYSA'

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/968,340

(22) Filed: Sep. 30, 2001

(51) Int. Cl.[7] ..... A01H 5/00
(52) U.S. Cl. ..... Plt./307
(58) Field of Search ..... Plt./307

(56) References Cited

U.S. PATENT DOCUMENTS

PP8,773 P * 6/1994 Fruehwirth ..... Plt./307

PP11,229 P * 2/2000 Fruehwirth ..... Plt./307

OTHER PUBLICATIONS

UPOV ROM GTITM Computer Database, GTI Jouve Retrieval Software 2002/02 Citation(s) for 'Eckalysa'.*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Poinsettia plant named 'Eckalysa', characterized by its inflorescences with large horizontally-orientated bright red-colored flower bracts; dark green-colored leaves with red-colored petioles; uniform and mounded plant habit; early flowering; and good post-production longevity.

1 Drawing Sheet

BOTANICAL CLASSIFICATION

*Euphorbia pulcherrima.*

BACKGROUND OF THE INVENTION

The present Invention relates to a new and distinct cultivar of Poinsettia plant, botanically known as *Euphorbia pulcherrima* Willd., and hereinafter referred to by the name 'Eckalysa'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia orginated from a cross made by the Inventor of the *Euphorbia pulcherrima* Willd. cultivar Eckabia, disclosed in U.S. Plant Pat. No. 11,229, as the female, or seed, parent, with the *Euphorbia pulcherrima* Willd. cultivar 559, disclosed in U.S. Plant Pat. No. 8,773, as the male, or pollen, parent. The cultivar Eckalysa was discovered and selected by the Inventor as a flowering plant within the progeny of the stated cross in a controlled environment in Encinitas, Calif., in December, 1996. The selection of this plant was based on its attractive flower bract colors and good plant form and substance.

Asexual reproduction of the new Poinsettia by terminal cuttings taken at Encinitas, Calif., since January, 1998, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckalysa'. These characteristics in combination distinguish 'Eckalysa' as a new and distinct cultivar:

1. Inflorescences with large horizontally-orientated bright red-colored flower bracts.

2. Dark green-colored leaves with red-colored petioles.

3. Uniform and mounded plant habit.

4. Early flowering, natural season flower maturity date is December 1 for plants grown in Encinitas, Calif.; response time, about 9 weeks.

5. Good post-production longevity.

Plants of the new Poinsettia can be compared to plants of the female parent, the cultivar Eckabia. In side-by-side comparisons conducted in Encinitas, Calif., plants of the new Poinsettia differed primarily from plants of the cultiavr Eckabia in the following characteristics:

1. Plants of the new Poinsettia were more vigorous and less compact than plants of the cultivar Eckabia.

2. Leaves of plants of the new Poinsettia were darker green than leaves of plants of the cultivar Eckabia.

3. Plants of the new Poinsettia flowered about one week earlier than plants of the cultivar Eckabia.

Plants of the new Poinsettia can be compared to plants of the male parent, the cultivar 559. In side-by-side comparisons conducted in Encinitas, Calif., plants of the new Poinsettia differed primarily from plants of the cultivar 559 in the following characteristics:

1. Plants of the new Poinsettia were broader than plants of the cultivar 559.

2. Plants of the new Poinsettia had shorter leaf petioles than plants of the cultivar 559.

3. Flowers bracts of plants of the new Poinsettia were larger than flower bracts of the cultivar 559.

4. Plants of the new Poinsettia flowered about one week earlier than plants of the cultivar 559.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The top photograph comprises a side perspective view of a typical flowering plant of 'Eckalysa' grown in a 16.5-cm container.

The lower photograph is a close-up view of typical leaves and flower bracts of 'Eckalysa' (left) and '559' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the winter under commercial practice in a polyethylene-covered greenhouse with day temperatures about 24° C., night temperatures about 19° C., and light levels about 4,000 foot-candles. Single plants were grown in 16.5-cm pots and pinched once. Plants were flowered under natural season short day/long night conditions. Plants were about 18 weeks from unrooted cuttings when the photographs and the detailed botanical description were taken.

In the following description, color references are made to The Royal Horticultural Society Colour Chart except where general terms of ordinary dictionary significance are used.

Botanical classification: *Euphorbia pulcherrima* Willd. cultivar Eckalysa.

Parentage:

*Female parent.*—*Euphorbia pulcherrima* Willd. cultivar Eckabia, disclosed in U.S. Plant Pat No. 11,229.

*Male parent.*—*Euphorbia pulcherrima* Willd. cultivar 559, disclosed in U.S. Plant Pat. No. 8,773.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous and freely-branching.

Plant description:

*Plant form.*—Inverted triangle, top of plant rounded and mounding.

*Growth habit.*—Upright and uniform plant habit. Moderate vigor.

*Plant height.*—About 28 cm.

*Plant diameter or spread.*—About 32 cm.

*Lateral branch description.*—Quantity: About five lateral branches develop after pinching. Length: About 23.5 cm. Diameter: About 7 mm. Internode length: About 1.75 cm. Color: 146A.

*Foliage description.*—Arrangement: Alternate, single. Quantity of leaves per lateral branch: About nine. Length: About 12.2 cm. Width: About 11 cm. Shape: Elliptic with irregular lobing. Apex: Acuminate. Base: Acute. Margin: Entire with irregular lobing. Venation pattern: Pinnate. Texture: Upper surface: Glabrous. Lower surface: Slightly pubescent. Surface: Slightly puckered. Color: Young and fully expanded foliage, upper surface: 147A. Young and fully expanded foliage, lower surface: 147B. Venation, upper surface: 147B. Venation, lower surface: 147D. Petiole: Length: About 4 cm. Diameter: About 3 mm. Color: 183A.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Nothern Hemisphere. Flower initiation and development is induced under long nyctoperiod conditions. Response time, about 9 weeks; natural season flower maturity date is December 1 for plants grown in Encinitas, Calif.

*Post-production longevity.*—Plants of the new Poinsettia maintain good substance and bract color for about three to four weeks under interior conditions.

*Quantity of inflorescences per plant.*—One per lateral branch, about five.

*Inflorescence size.*—Diameter: About 34 cm. Height (depth): About 4 cm.

*Flower bracts.*—Quantity of flower bracts per inflorescence: About 24. Length, largest bracts: About 17.5 cm. Width, largest bracts: About 9.2 cm. Shape: Elliptic with irregular lobing. Apex: Acuminate. Base: Acute. Margin: Entire with irregular lobing. Texture, upper and lower surfaces: Glabrous, velvety. Surface: Slightly rugose. Orientation: Mostly horizontal to slightly drooping. Color: Developing or transitional bracts, upper surface: Irregular and random areas of brighter than 46A and 147A, then becoming mostly brighter than 46A. Developing or transitional bracts, lower surface: Irregular and random areas of 46B and 147B, then becoming mostly 46B. Fully developed bracts, upper surface: 46B to 46C; color does not fade with subsequent development. Fully developed bracts, lower surface: 51A. Venation, upper and lower surfaces: Same as ground color. Bract petiole: Length: About 3 cm. Diameter: About 2 mm. Color: 53A to 53B.

*Cyathia.*—Quantity: About 18 per corymb. Diameter of cyathia cluster: About 3 by 4 cm. Length: About 1.6 cm. Width: About 7 mm. Shape: Ovoid. Color: Immature: 144A. Mature: 144B to 144C. Peduncle: Length: About 3.5 mm. Diameter: About 2 mm. Aspect: Strong, erect. Color: 144B. Stamens: Stamen number: More than 20 per cyathium. Anther shape: Oval. Anther length: Less than 1 mm. Anther color: 59A. Amount of pollen: Scarce. Pollen color: 12B. Pistils: Pistil number: One per cyathium. Pistil length: About 1 cm. Stigma shape: Six-parted. Stigma color: 46A. Style length: About 4 mm. Style color: 144B. Ovary color: 144B. Nectary number: One per cyathia. Nectary color: 23A.

Disease/pest resistance: Resistance to pathogens and pests common to Poinsettias has not been observed on plants grown under commercial conditions.

It is claimed:

1. A new and distinct cultivar of Poinsettia plant named 'Eckalysa', as illustrated and described.

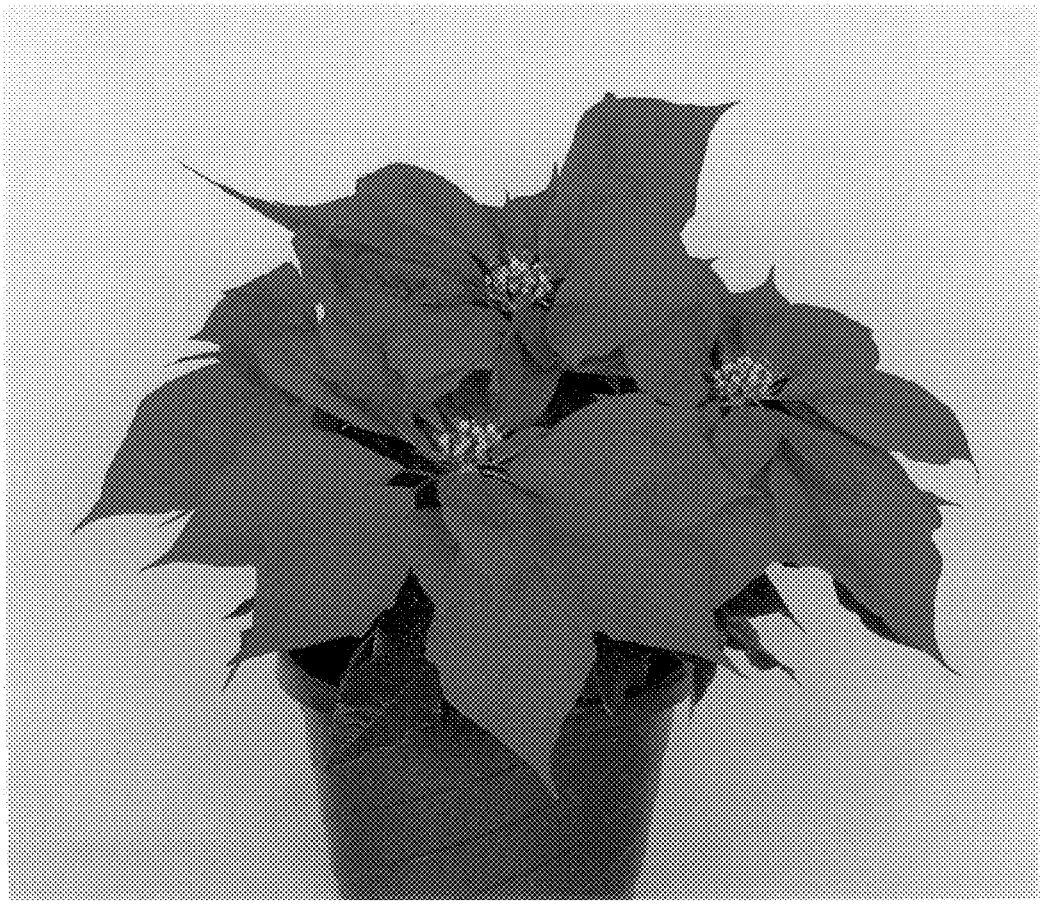
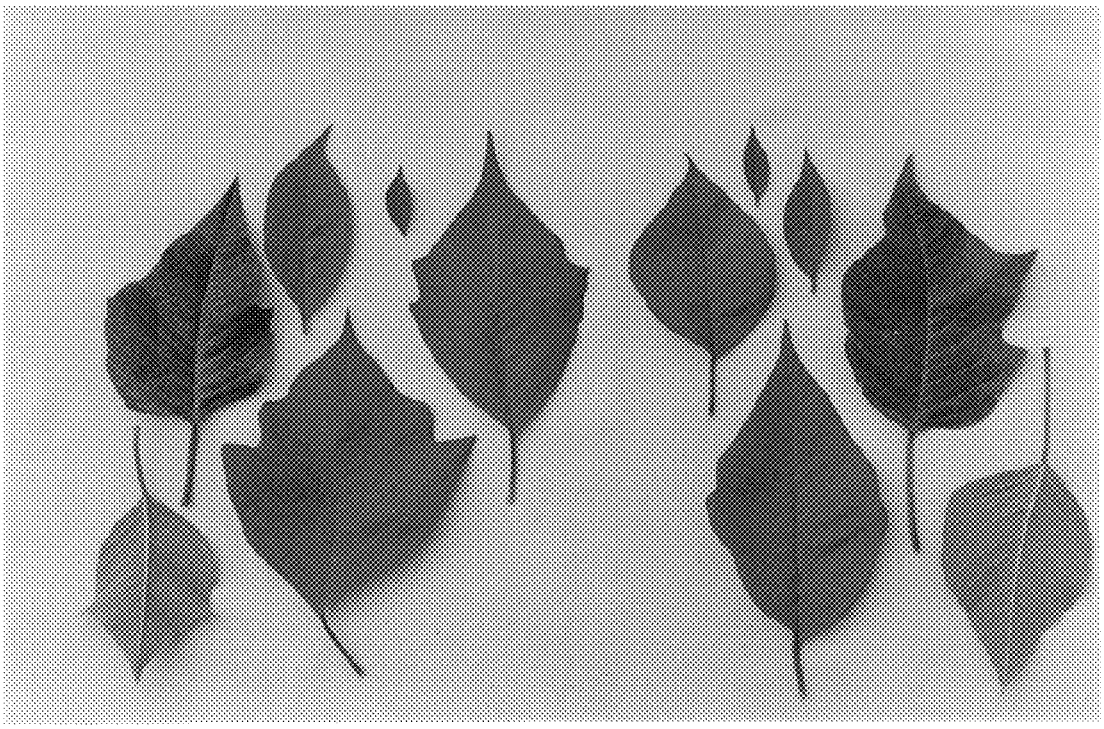

* * * * *